United States Patent [19]

Aufdermarsh, Jr.

[11] 3,997,592

[45] Dec. 14, 1976

[54] PREPARATION OF AQUEOUS DISPERSIONS OF BLOCKED AROMATIC POLYISOCYANATES

[75] Inventor: Carl Albert Aufdermarsh, Jr., Newark, Del.

[73] Assignee: E. I. Du Pont de Nemours and Company, Wilmington, Del.

[22] Filed: Nov. 24, 1975

[21] Appl. No.: 634,641

[52] U.S. Cl. .................. 260/471 C; 260/29.2 TN; 260/29.3; 260/453 AR
[51] Int. Cl.² ..................................... C07C 125/06
[58] Field of Search ............. 260/471 C, 77.5 TB, 260/29.2 TN

[56] References Cited

UNITED STATES PATENTS 3,268,467  8/1966  Rye et al. .................. 260/29.3

*Primary Examiner*—Lewis Gotts
*Assistant Examiner*—Dolph H. Torrence

[57] ABSTRACT

Aqueous dispersions of aromatic polyisocyanates blocked with phenolic compounds are prepared by mixing the polyisocyanate and an aqueous solution containing an excess of the phenolic compound in the presence of a basic catalyst at a temperature above the melting point of the polyisocyanate.

8 Claims, No Drawings

PREPARATION OF AQUEOUS DISPERSIONS OF BLOCKED AROMATIC POLYISOCYANATES

SUMMARY OF THE INVENTION

This invention relates to a process for the preparation of aqueous dispersions of aromatic polyisocyanates blocked with phenolic compounds. Such dispersions are suitable for use in the formation of a single dip coating on polyester substrates and such coatings cause the polyester to adhere to rubber.

BACKGROUND

It is known to prepare phenol blocked aromatic polyisocyanates by reacting the components in an organic solvent. It is also known to form aqueous dispersions of blocked isocyanates by mixing an aqueous solution of phenol and a solution of a polyisocyanate dissolved in a water soluble organic solvent. The present invention directly produces an aqueous dispersion of a blocked polyisocyanate without the use of an organic solvent.

DETAILED DESCRIPTION OF THE INVENTION

The present invention comprises a process for the preparation of an aqueous dispersion of a phenolic compound-blocked aromatic polyisocyanate. This aqueous dispersion is obtained by intimately mixing an aromatic polyisocyanate and an aqueous solution of a phenolic compound in the presence of an effective amount of a basic catalyst at a temperature above the melting point of the polyisocyanate. A preferred temperature range is from 25° to 90° C. The reaction rate is temperature dependent, but the reaction will be substantially complete in from 2 to 60 minutes. In the preferred process the polyisocyanate is added to the solution of the phenolic compound.

The number of moles of the phenolic compound employed should be at least equal to the number of equivalents of isocyanate groups present, and the number of moles of phenolic compound may be as much as 8 times the number of equivalents of isocyanate groups. The preferred range of moles of phenolic compound per equivalent isocyanate group is about 1.01 to about 5.

An effective amount of basic catalyst is usually about 0.01 to 1 wt. percent based on the amount of water present. Suitable bases include any alkali metal hydroxide, tertiary aliphatic amines such as triethyl amine, diethyl cyclohexyl amine, and guanidines such as tetramethylguanidine.

The phenolic compound employed as the blocking agent can be phenol, resorcinol, $C_1$ to $C_{15}$ alkyl derivatives of phenol and $C_1$ to $C_{15}$ derivatives of resorcinol.

Aromatic polyisocyanates are a well known class of compounds, and any of these compounds may be used herein, but the preferred compounds are 4,4'-methylene diphenylisocyanate, toluene-2,4-diisocyanate, benzene-1,3-diisocyanate, diphenylether-2,4,4'-triisocyanate, and triphenylmethane-4,4',4''-triiisocyanate. 4,4'-Methylene diphenylisocyanate is the preferred compound.

It is desirable when carrying out the blocking reaction to have present in the mixture a surfactant. Suitable surfactants may be either anionic or nonionic. Suitable anionic surfactants are sodium dioctylsulfosuccinate and sodium dioctyldecylsulfosuccinate. Suitable nonionic surfactants include the olefin/vinyl pyrrolidone copolymers, sold commercially as "Ganex" V polymers. U.S. Pat. No. 3,591,568 to Farber describes these materials in more detail. The surfactant can be present in the reaction mixture in the amount of about 1–10% by weight of the blocked isocyanate.

Since the mixing of the aromatic polyisocyanate and the aqueous solution of a phenol compound takes place under conditions such that the polyisocyanate is in the liquid state, that is, at a temperature above the melting point of the polyisocyanate, it is usually preferred to have the temperature of both the aqueous solution of the phenol compound and the aromatic polyisocyanate above the melting point of the polyisocyanate. Since it is usually preferred to add the aromatic isocyanate to the aqueous solution, the temperature of the aqueous solution should preferably be at least about 1° to 5° C. above the melting point of the aromatic polyisocyanate.

It is highly desirable that the mixing of the ingredients be carried out quickly and efficiently. High speed mixers available commercially are satisfactory to achieve the desired good agitation and intimate mixture.

The particle size of the precipitate formed can be regulated by addition of greater or lesser amounts of surfactants and by agitation rate.

The dispersions formed by the present invention may be used to form single dip coating solutions for polyesters. If the phenolic compound employed in the formation of the dispersion is resorcinol, an aqueous solution of formaldehyde is merely added with mixing to the dispersion; a resorcinol-formaldehyde resin thus directly forms as the resorcinol was added in excess of that needed to block the isocyanate. On the other hand, if phenol is employed in blocking the isocyanate, then an amount of resorcinol is first added to the dispersion such that in the final dispersion the weight ratio of resorcinol-formaldehyde resin to blocked aromatic polyisocyanate is in the range of about 0.2 to 1 to about 1.5 to 1.

The formation of the resorcinol-formaldehyde resin in the dispersion of blocked isocyanate takes place on the addition of formaldehyde to the dispersion containing the resorcinol. This reaction is best carried out at a temperature in the range of about 25° to 50° C. The resorcinol is preferably present in a small molar excess over the amount of formaldehyde present.

The final coating solution must also contain a water insoluble polyepoxide and a rubber latex. These components are merely added in accordance with the conventional practices of the art as illustrated by U.S. Pat. No. 3,234,067. The weight ratio of polyepoxide present in the dispersion to amount of blocked isocyanate present should be about 0.1 to 1 to about 4 to 1. The amount of rubber latex solids present in the dispersion should be from about equal to the amount of resorcinol-formaldehyde resin present to about 6 times the amount of resorcinol-formaldehyde resin present.

The coating solution will contain about 6 to 24% by weight total solids. It may be applied in the conventional manner to the polyester substrate. After application the coating is heated to above about 200° C. for 0.5 to 15 minutes to remove the water and cure the coating. Usually the polyester substrate is kept under tension to prevent shrinkage. Thereafter rubber is applied and cured.

The single dip coating composition contains about 0.01 to 1 wt. percent alkali metal hydroxide, based on the weight of the water present.

In the examples which follow, all parts and percentages are in parts by weight and all temperatures are in degrees centigrade unless otherwise specified.

EXAMPLES

EXAMPLE 1

A 5-liter round-bottom flask was charged with 400 g resorcinol, 1800 ml. water, 3.0 g sodium hydroxide pellets, 30 g sodium dioctylsulfosuccinate (100% active, sold as Aerosol OT by American Cyanamid), and a droplet of silicon complex antifoaming agent (sold as Dow "Antifoam" C by Dow Chemical Co.). The mixture became homogeneous while being warmed to 45° C. with stirring. To the warm vigorously agitated solution was added 200 g molten 4,4'-methylene diphenylisocyanate at about 45° C. Addition was completed in one minute. A precipitate appeared and the temperature rose to a peak of 52° C. after eight minutes and then began to subside. After about an hour the reaction mixture was cooled and the precipitate collected by suction filtration. The cake of precipitate was washed with water, air dried, and then dried in a vacuum desiccator to yield a white powder weighing 362 g. The product was identified as the bis resorcinol adduct of the isocyanate (94% pure) by its infrared spectrum, melting point, nitrogen analysis and solubility in acetone. The product contained about 5% of a resorcinol-isocyanate polymer, and less than 1% of an isocyanate-based polyurea.

EXAMPLE 2

A solution of 390 g resorcinol, 27.3 g nonylphenol (principally p-nonylphenol with about 3% ortho isomer and 4% 2,4-dinonylphenol sold by Rohm and Haas Co.), 30.9 g sodium dioctyl sulfosuccinate (75% active, sold as Aerosol OT by American Cyanamid), 58.5 ml 5% solution hydroxide solution, and a drop of Dow Antifoam C in 1700 ml. deaerated water was prepared under nitrogen in a 5-liter roundbottom flask. The solution was warmed to about 48° C. and poured into a 4-liter steel beaker into which an Eppenbach Homomixer was inserted. Through a dip leg leading to the base of the Homomixer was added 195 g molten 4,4'-methylene diphenylisocyanate (at about 45° C.) while the mixer was operating at about 80% of maximum speed. Addition was completed in less than one minute. A milky white dispersion formed immediately, and the temperature rose rapidly to about 58° C., then started to fall. The dispersion was cooled to 25° C. and 600 g were filtered as described in Example 1. The product was isolated in 96.5% yield and consisted of 95.9% of a mixture of the resorcinol and nonylphenol adducts of the isocyanate.

To the remaining 1802 g of dispersion was added 77 g 37% aqueous formaldehyde and the mixture stirred one hour. The mixture was used in combination with a micronized epoxy cresol novolak resin (sold as ECN 9595 by Ciba Geigy) and a butadiene/styrene/2-vinyl pyridine latex to prepare a single dip adhesive. When tested as an adhesive for polyester tire cord in a standard rubber compound, adhesion was excellent.

EXAMPLE 3

To a solution of 44.6 parts of phenol and 0.04 parts of diethylcyclohexylamine in 142.3 parts of water was added 0.95 parts of an alkylated polyvinylpyrrolidone (Ganex V-220, avg. mol. wt.~8600, sold by GAF Corp.) dissolved in 3.2 parts of n-heptane. This aqueous dispersion was heated to 65°–70° C. and 59.2 parts of 4,4'-methylene diphenylisocyanate was added over a one hour period. The reaction mass was cooled to 30 ± 5° C. and the wet product isolated by filtration. Drying to constant weight at 70°–80° C. and 25'' Hg gave 100 parts dry product. Analysis showed the product to be about 90% bis phenol adduct of the isocyanate and about 10% blocked urea and biurets.

I claim:

1. A process for the production of an aqueous dispersion of an aromatic polyisocyanate blocked with a phenolic compound which comprises mixing (a) an aromatic polyisocyanate and (b) an aqueous solution containing a dissolved phenolic compound selected from the class consisting of phenol, resorcinol and $C_1$ to $C_{15}$ alkyl derivatives of phenol and $C_1$ to $C_{15}$ alkyl derivatives of resorcinol, at a temperature above the melting point of the polyisocyanate, in the presence of an effective amount of a basic catalyst, the number of moles of phenolic compound being at least equal to the number of equivalents of isocyanate groups present.

2. The process of claim 1 in which the mixing takes place at a temperature between about 25° and 90° C.

3. The process of claim 2 in which the basic catalyst is an alkali metal hydroxide, and the basic catalyst is present in the amount of about 0.01 to 1.0 wt. percent based on the amount of water present.

4. The process of claim 1 in which a surfactant is present in aqueous solution of phenolic compound.

5. The process of claim 4 in which the surfactant is nonionic or anionic.

6. The process of claim 1 in which the aromatic polyisocyanate is selected from the class consisting of 4,4'-methylene diphenylisocyanate, toluene-2,4-diisocyanate, benzene-1,3-diisocyanate, diphenylether-2,4,4'-triisocyanate, and triphenylmethane-4,4'4''-triisocyanate.

7. The process of claim 6 in which the phenolic compound is resorcinol.

8. The process of claim 6 in which the phenolic compound is phenol.

* * * * *